United States Patent [19]  [11] 4,229,463
Kathawala  [45] Oct. 21, 1980

[54] UNSATURATED FATTY ACID HYDRAZIDES

[75] Inventor: Faizulla G. Kathawala, West Orange, N.J.

[73] Assignee: Sandoz, Inc., E. Hanover, N.J.

[21] Appl. No.: 881,780

[22] Filed: Feb. 27, 1978

[51] Int. Cl.² ............... A01N 9/22; A61K 31/40; C09F 5/00; C07D 209/12
[52] U.S. Cl. .................. 424/274; 424/320; 424/324; 260/404.5; 260/326.13 B
[58] Field of Search ........... 260/404.5 H, 326.13 B; 424/274, 320, 324

[56] References Cited
U.S. PATENT DOCUMENTS 2,970,159  1/1961  Gutmann ............ 260/404.5
3,162,680  12/1964  Biel ................. 260/404.5
3,551,462  12/1970  Seki ................. 424/320
3,836,580  9/1974  Bruce ............... 260/326.13 R

OTHER PUBLICATIONS

Sumitomo Chemical Co., Derwent Report 27430R, (1970).

Primary Examiner—John F. Niebling
Attorney, Agent, or Firm—Gerald D. Sharkin; Richard E. Vila; Frederick H. Weinfeldt

[57] ABSTRACT

Mono- or poly-unsaturated fatty acid hydrazides, e.g. cis,-9-octadecenoic acid, 2-(o-methylphenyl)-hydrazide are useful as pharmaceutical agents and are obtainable by reacting a derivative, e.g. mixed anhydride, of a long chain unsaturated carboxylic acid with an appropriate hydrazine compound.

29 Claims, No Drawings

UNSATURATED FATTY ACID HYDRAZIDES

This invention relates to organic compounds and more particularly to unsaturated fatty acid hydrazides (and pharmaceutically acceptable acid addition salts thereof) and to pharmaceutical compositions containing such compounds, as well as to the pharmaceutical use of such compounds.

The compounds of this invention are conveniently represented by the formula I:

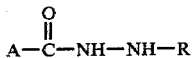

wherein

A is the residue of a fatty acid minus the carboxylic function, and has from 7 to 23 carbon atoms and from 1 to 4 ethylenically unsaturated positions; and R is:

(a) an aralkyl radical of the structure

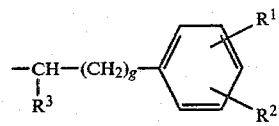

wherein g is 0 or 1;
wherein
$R^1$ is a hydrogen atom, halo having an atomic weight of from about 19 to 80, ie. fluoro, chloro or bromo, alkoxy having from 1 to 3 carbon atoms, eg methoxy; or alkyl having from 1 to 3 carbon atoms, eg methyl;

$R^2$ is a hydrogen atom, alkyl having from 1 to 3 carbon atoms, alkoxy having from 1 to 3 carbon atoms, or halo having an atomic weight of from about 19 to 36, ie fluoro or chloro; and $R^3$ is (i) a hydrogen atom, a phenyl radical of the structure (ii)

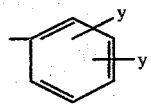

wherein
y is a hydrogen atom, halo having an atomic weight of from about 19 to 80, ie. fluoro, chloro or bromo, alkoxy having from 1 to 3 carbon atoms, eg methoxy; or alkyl having from 1 to 3 carbon atoms, eg methyl; and
y' is a hydrogen atom, alkoxy having from 1 to 3 carbon atoms, alkyl having from 1 to 3 carbon atoms, or halo having an atomic weight of from about 19 to 36, ie fluoro or chloro; or
a benzyl radical of the formula (iii)

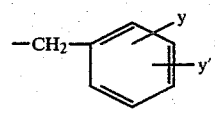

wherein y and y' are as defined above; or (iv) alkyl having from 1 to 8 carbon atoms; or R is:

(b) a phenyl radical of the structure

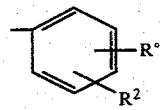

wherein $R^2$ is as defined above, and $R^o$ is a hydrogen atom, halo having an atomic weight of from about 19 to 80, ie fluoro, chloro or bromo, alkyl having from 1 to 3 carbon atoms; alkoxy having from 1 to 3 carbon atoms; or a radical of the structure $R^f$:

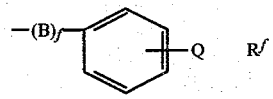

in which
B is —$CH_2$— or —O—;
f is 0 or 1; and
Q is a hydrogen atom, halo having an atomic weight of from about 19 to 80, alkoxy having from 1 to 3 carbon atoms, or alkyl having from 1 to 3 carbon atoms;
or R is:

(c) an indolyl radical of the structure:

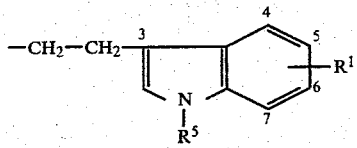

wherein
$R^1$ is as defined above, and
$R^5$ is a hydrogen atom, alkyl having from 1 to 8 carbon atoms or benzyl (unsubstituted);
or R is (d) a benzocycloalkyl nucleus of the structure:

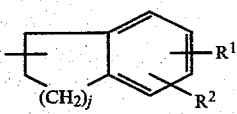

wherein
$R^1$ and $R^2$ are as defined above; and
j is a whole integer of from 1 to 4.

Compounds I may be obtained by acylation (process a) of a hydrazine of formula II:

$$H_2N-NH-R \qquad (II)$$

in which R, is as defined above, with an unsaturated-long chain fatty acid or derivative thereof corresponding to the moiety —A as defined above. Such "acylation" may be carried out by means conventionally employed in converting a hydrazino function to its corresponding hydrazide, such as are reported in the literature.

The acylation (process a) may conveniently be carried out by a mixed anhydride technique (process a1) wherein a compound II is treated with a mixed anhydride of the formula III:

$$A-\overset{O}{\underset{\|}{C}}-O-\overset{O}{\underset{\|}{C}}-OR^6 \qquad \text{III}$$

in which A is as defined above and $R^6$ is a lower unbranched alkyl having from 1 to 6 carbon atoms, at moderate temperatures, eg from about $-10°$ C. to $+35°$ C., in an inert organic medium, eg a chlorinated hydrocarbon, such as methylene chloride.

The mixed anhydrides (III) are obtainable by reacting (process b1) a free carboxylic acid of the formula IV:

$$A-\overset{O}{\underset{\|}{C}}-OH \qquad \text{IV}$$

wherein A is as defined above, with a chloroformate of the formula V, $$Cl-\overset{O}{\underset{\|}{C}}-OR^6 \qquad \text{V}$$

wherein $R^6$ is as defined above, in the presence of an acid acceptor, eg an organic base, such as triethylamine, at reduced temperatures, eg at from about $-10°$ to $+30°$ C., in an inert organic medium, eg a chlorinated hydrocarbon, such as methylene chloride.

Another convenient method of preparing compounds I comprises reacting (process a2) an acyl halide of the formula VI $$A-\overset{O}{\underset{\|}{C}}-X \qquad \text{VI}$$

in which A is as defined above, and X is either chloro or bromo, with a compound II (as defined above), in the presence of an acid acceptor, in an inert medium at moderate temperatures, eg from about 10° to 50° C. preferably at about 20° to 30° C.

The acyl halides (VI) may be prepared in the conventional manner, eg by treating (process b2) a corresponding compound IV (as defined above), with a halogenating agent capable of contributing a chlorine or bromine atom, eg thionyl chloride (or —bromide, as appropriate).

In the above-described processes, neither the media nor the temperature are critical to the reactions, and where the reactants or reagents are liquid, an excess thereof may serve as the reaction medium. If desired a compound II may be in the form of a water-soluble acid addition salt, for example the hydrochloride. The mixed anhydride (III) resulting from process b1 may conveniently be used in situ. That is to say that provided that the materials in the reaction mixture containing the mixed anhydride are not detrimental, they may be used directly for process a1) without recovery.

Reagents and reactants described herein, e.g., compounds II, III, IV, V, and VI are known and obtainable by known means, or where not known, may be obtained by adaptation of methods reported in the literature for the preparation of known analogs; many such compounds being commercially available.

With respect to R, when it is of type (a) or (b) and $R^o$ is not $R^f$, it is preferred that when $R^1$, $R^o$ or y is other than a hydrogen atom and $R^2$ (or y') is a hydrogen atom, that $R^o$, or $R^1$, or y be located at the 2-position; and that when $R^2$ (or y') is also other than a hydrogen atom that $R^1$ or $R^o$ and $R^2$ (or y and y') are the same, and it is additionally preferred that they be located at the 2- and 6-positions of the phenyl ring. When R is of type (a) where $g=1$, and $R^3$ is of type (iii), then R can be an α-(benzyl)-phenylethyl radical.

With particular respect to the substituent $R^o$ when it is a radical $R^f$, it will be appreciated that when $B=CH_2$ and $f=1$, then the radical $R^f$ is of the benzyl type. When $B=$oxygen and $f=1$, then the radical $R^f$ is of the phenoxy-type. When $f=$zero, then the radical $R^f$ is of the phenyl-type. Hence, when R is of type (b) and $R^o$ is of type $R^f$ where $f=$zero, then R can be a biphenylyl radical. The radical $R^f$ is preferably at the para-position. When Q is other than a hydrogen atom, it is preferably at the para-position.

With respect to R, when it is of type (c), it is preferred that when $R^1$ is other than a hydrogen atom, it be located at the 5-position of the indole nucleus.

With respect to R when it is of type (d) it is preferred that when $R^1$ is other than a hydrogen atom, that it be located at a carbon atom ortho to the ring junction; and that when $R^2$ is also other than a hydrogen, it is preferred that it be the same as $R^1$, and it is additionally preferred that it be in para-relationship to $R^1$. It is additionally preferred that the amide group be linked to a carbon of the cycloalkyl moiety which is directly bonded to a ring junction carbon. It is also preferred that j be 1, ie, that the benzocycloalkyl nucleus be indanyl, and particularly 1-indanyl.

Embodiments of this invention are Compounds I in which A is of the formula:

$$CH_3-(CH_2)_r-(CH=CH)_s-(CH_2)_t- \qquad \text{(A1)}$$

or $$CH_3-(CH_2)_n-(CH=CH-CH_2)_m-(CH_2)_p- \qquad \text{(A2)}$$

wherein when A is (A1) then
 $r=1$ to 10,
 $s=1$ to 4, and
 $t=4$ to 9;
particularly where $r=5$ or 7, $s=1$, and $t=7$; and when A is (A2) then
 $n=1$ to 4,
 $m=2$ to 4, and
 $p=2$ to 7;
particularly where
 $n=1$ or 4, $m=$from 2 to 4 and $p=2$ or 6.

The total number of carbon atoms in (A1) or (A2) conform to the definition of A, above. That is to say that since A is the residue of an acid having from 8 to 24 carbons; A has from 7 to 23 carbons and from 1 to 4 unsaturated positions. Radicals A which are unbranched are preferred. Also generally preferred are the fatty acid derivatives of the natural fatty acid order, ie those in which A represent an odd number of carbon atoms of from 7 to 23 and accordingly A—C=O represent an even number of carbon atoms of from 8 to 24.

Examples of acids suitable to provide A are given in tables I and II below:

TABLE I

| carbons in A—C=O | A = A1) | | | |
|---|---|---|---|---|
| | r | s | t | acid |
| 16 | 5 | 1 | 7 | palmitoleic |
| 18 | 7 | 1 | 7 | oleic |

TABLE I-continued

A = A1)

| carbons in A—C=O | r | s | t | acid |
|---|---|---|---|---|
| 18 | 10 | 1 | 4 | petroselenic |
| 18 | 5 | 1 | 9 | vaccenic |
| 18 | 3 | 3 | 7 | punicic (or eleostearic) |
| 18 | 1 | 4 | 7 | parinaric |
| 20 | 9 | 1 | 7 | gadoleic |
| 22 | 9 | 1 | 9 | cetoleic |

TABLE II

A = A2)

| carbons in A—C=O | n | m | p | acid |
|---|---|---|---|---|
| 18 | 4 | 2 | 6 | linoleic |
| 18 | 1 | 3 | 6 | linolenic |
| 20 | 4 | 4 | 2 | arachidonic |

Those compounds I wherein A is derived from oleic, linoleic, linolenic or arachidonic acids are particularly preferred.

It will be appreciated that the unsaturated acids which provide the moiety A occur in isomeric forms due to the presence of the one or more unsaturated positions. The particular isomeric form of the A moiety in a parent acid will remain the same in the resulting Compound I, since the structural configuration of the A moiety is not changed by the processes yielding compounds I. Compounds I wherein the hydrogen atoms on the pair of carbons of each unsaturated position of the A-moiety are in the cis configuration are preferred.

Particular embodiments of this invention are the compound cis-9-octadecenoic acid, 2-(o-methylphenyl)-hydrazide as well as pharmaceutical compositions containing said compound as well as the use of said compound and compositions containing said compound as described herein.

The final products and intermediate compounds described herein may be recovered and refined, where such is desired, by conventional means, such as by crystallization, distillation or chromatographic techniques such as column or thin layer chromatography.

STATEMENT OF UTILITY

The compounds of formula I of this invention are useful as pharmaceutical agents in animals. In particular, the compounds of the formula I are useful in controlling the chloresterol ester content of mammalian arterial walls and are therefore particularly indicated for use as anti-atherosclerotic agents, ie. agents useful in the prophylactic treatment of atherosclerois and in the controlling of atherosclerotic conditions due to chloresterol ester accumulation in the arterial walls. Such ability of the compounds of the formula I is indicated by known test procedures in which the total cholesterol ester content of cultured cells is shown to be reduced by a test compound, as compared to untreated cells, and carried out, for example, by the following procedures:

(A) Cell culture

Rhesus monkey smooth muscle cells (from the arterial, eg aorta, wall) obtained by the method of K. Fisher-Dzoga et al (Experimental and Molecular Pathology 18, 162–176 (1973)) are routinely grown in 75 cm$^2$ tissue culture flasks using Minimum Essential Medium (Eagle) supplemented with 10% fetal bovine serum. For testing a 75 cm$^2$ flask with a near confluent cell growth is selected. The cells are removed from the flask surface by mild enzymatic treatment with pronase. After centrifugation and decanting the enzyme solution, the cell pellet is resuspended in an appropriate volume of media for seeding the desired number of 60 mm tissue culture dishes. Five (5) ml of the diluted cell suspension are pipetted into each dish. After seeding, the dishes are labelled with the cell type, date and flask number of origin and incubated at 37° C. in approximately 5% $CO_2$ atmosphere in a high humidity incubator. When the cultures are confluent, the actual drug testing is begun. Test compounds are routinely solubilized in 100% ethanol. An equivalent amount of ethanol is added to control groups as well. The tissue culture dishes are randomly divided into groups. To one group, hyperlipemic rabbit serum (HRS) is added at 5% by volume (control). To the remaining groups, 5% HRS and 1 mg per 100 ml of media of the test compound are added. The dishes are returned to the incubator for an additional 24 hours. All operations through to the final incubation are performed using sterile technique in a laminar flow hood. After the incubation period, the dishes are microscopically observed with the Zeiss Axiomat with phase contrast optics and the conditions of the cultures are recorded; especially in regard to the size, number and configuration of cytoplasmic inclusions and to cellular morphology. The media is removed from the cultures and 0.9% sodium chloride solution is added. The cells are removed from the flasks with the aid of a rubber policeman and transferred to a conical graduated centrifuge tube. The cells are washed three times by suspending in an isotonic salt solution, centrifuging at 800×g for 10 minutes and aspirating the supernatant fluid.

(B) Cell extraction procedure

An appropriate volume of isopropyl alcohol (about 1 ml/mg protein) is then added to the cell pellet and the sample sonicated with a micro probe (140×3 mm) for 10 seconds with a "LO" setting of 50 on a Bronwell Biosonik IV. After centrifugation for 15 minutes at 800×g, the clear supernatant is decanted and an aliquot taken for cholesterol analysis.

The residue is dissolved in 0.1 N sodium hydroxide and an aliquot taken for protein determination by the method of Lowry, et al. (J. Biol. Chem. 193, 265; 1951).

(C) Assay

Free cholesterol: The isopropyl alcoholic solutions of standards, samples and blank (isopropyl alcohol alone) are treated in a similar manner. An aliquot of 0.4 ml of free reagent (Reagent A, Table 1 below) is added to a 10×75 mm disposable glass test tube to which 20 $\mu$l of the isopropyl alcoholic solution is added and mixed. After standing at room temperature for approximately 5 minutes, 0.8 ml of 0.5 N sodium hydroxide (Reagent C, Table 1) is added and mixed. The fluorescence is measured with an Aminco-Bowman spectrophotofluorometer with an excitation wavelength of 325 nm and emission wavelength of 415 nm. A 1 cm light path cuvette is used with a xenon lamp, an IP28 photomultiplier tube and 2 mm slits.

Total cholesterol: The same procedure described above for free cholesterol is followed for total cholesterol except that the total reagent (Reagent B, Table 1) is used instead of the free reagent and the samples are incubated for 20 minutes at 37° C. before the addition of the 0.5 N sodium hydroxide solution (Reagent C, Table 1).

Alternatively, the assay for cholesterol, ie Step C (above) obtained from Steps A and B, may be carried out by the method of Ishikawa et al (J. Lipid Res. 15, 286; 1974).

The amount of cholesterol ester is found by subtracting the amount of free cholesterol from the total cholesterol content of the cells determined by the assay. A finding of a lower amount of cholesterol ester in the group of cells to which test compound was added, as compared to the control group (untreated) shows that the test compound is active in reducing the cholesterol ester in the cells.

TABLE 1

Composition of Reagents for Cholesterol Determination

| | | |
|---|---|---|
| A. Free Cholesterol Reagent | | |
| Sodium phosphate buffer pH 7.0 | .05 | M |
| Cholesterol oxidase | .08 | U/ml |
| Horseradish peroxidase | 30. | U/ml |
| p-Hydroxyphenylacetic acid | .15 | mg/ml |
| B. Total Cholesterol Reagent | | |
| Sodium phosphate buffer pH 7.0 | .05 | M |
| Cholesterol ester hydrolase | .08 | U/ml |
| Cholesterol oxidase | .08 | U/ml |
| Horseradish peroxidase | 30. | U/ml |
| Sodium taurocholate | 5. | mM |
| Carbowax-6000 | .17 | mM |
| p-Hydroxphenylacetic acid | .15 | mg/ml |
| C. Sodium Hydroxide Solution | | |
| | .5N | |

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

Furthermore, the compounds of formula I may be similarly administered in the form of their non-toxic pharmaceutically acceptable acid addition salts. Such salts possess the same order of activity as the free base, are readily prepared by reacting the free base with an appropriate acid and accordingly are included within the scope of the invention. Representative of such salts are the mineral acid salts, such as the hydrochloride, hydrobromide, sulfate, phosphate and the like and the organic acid salts such as the benzoate, acetate, maleate, fumarate, p-toluenesulfonate, benzenesulfonate and the like.

The antiatherosclerotic effective dosage of active ingredient employed for the reduction of cholesterol ester content in the arterial walls of a mammal may vary depending on the particular compound employed, the mode of administration and the severity of the condition being treated. However, in general, satisfactory results are obtained when the compounds of formula I are administered at a daily dosage of from about 2 milligrams to about 500 milligrams per kilogram of animal body weight, preferably given in divided doses two to four times a day, or in sustained release form. For most large mammals, the total daily dosage is from about 100 milligrams to about 5,000 milligrams preferably from about 100 milligrams to 2,000 milligrams. Dosage forms suitable for internal use comprise from about 25 to 2,500 milligrams of the active compound in intimate admixture with a solid or liquid pharmaceutically acceptable carrier. Solid carriers include starch, lactose and kaolin, while liquid carriers include sterile water, polyethylene glycols and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants eg vitamin E, ascorbic acid, BHT and BHA.

The preferred pharmaceutical compositions from the stand-point of ease of preparation and administration are solid compositions, particularly tablets and hard-filled or liquid-filled capsules.

A representative formulation for administration orally three times a day prior to feeding in the treatment of atherosclerosis is a gelatin capsule prepared by conventional techniques to contain the following

| Ingredient | Weight (in Mg.) |
|---|---|
| cis-9-octadecenoic acid, 2-(o-methylphenyl)-hydrazide | 300 |
| corn oil | 500 |

As is the present understanding in the art, controlling the total cholesterol content of an arterial wall by inhibiting the accumulation thereof by reducing the cholesterol ester content thereof, advantageously inhibits the formation of plaques in the arterial wall.

The following examples are illustrative of the invention. All temperatures are centigrade and room temperature is 20° to 30° C., unless indicated otherwise.

EXAMPLE 1 cis,cis-9,12-octadecadienoic acid, 2-benzyl-hydrazide

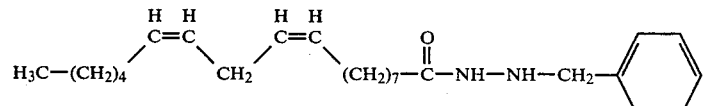

To a solution of 7.0 g linoleic acid in 250 ml methylenechloride cooled to −20° is added first 2.5 g triethylamine and then dropwise 2.7 g ethyl chloroformate. The reaction mixture is allowed gradually to come to room temperature and stirred for 2 hours. There is then added 5.0 g triethylamine followed by 4.9 g benzylhydrazine dihydrochloride and the reaction mixture then stirred for 16 hours. Thereafter the reaction mixture is extracted five times with portions of 2 N hydrochloric acid, then once with 2 N aqueous sodium hydroxide solution and washed extensively with saturated aqueous sodium chloride. The organic phase is then dried with anh. sodium sulphate, filtered and the filtrate evaporated i.v. to dryness. The residue is then chromatographed over silica gel, with chloroform as the eluent. The desired fractions* are collected, and evaporated i.v. to dryness to yield the title product as a viscous oil.

*indicated by thin layer chromatography of samples to contain reaction product free of starting material.

EXAMPLE 2

Repeating the procedure of Example 1, but using in place of the linoleic acid used therein, an approximately equivalent amount of:
(a) oleic acid;
(b) linolenic acid;
(c) palmitoleic acid; or
(d) arachidonic acid; there is accordingly obtained, respectively:
(a) cis-9-octadecenoic acid, 2-benzyl-hydrazide
(b) cis,cis,cis-9,12,15-octadecatrienoic acid, 2-benzyl-hydrazide
(c) cis-9-hexadecenoic acid, 2-benzyl-hydrazide; and
(d) cis,cis,cis,cis-5,8,11,14-eicosate-traenoic acid, 2-benzyl-hydrazide.

EXAMPLE 3

Repeating the procedure of Example 1, but using in place of the benzylhydrazine dihydrochloride used therein an approximately equivalent amount of the following amino compounds (as Compounds II) in the free or a hydrochloric acid addition salt form thereof:
(a) o-methylphenyl hydrazine;
(b) 2,6-dichlorophenyl hydrazine; or
(c) 2-chlorophenyl hydrazine; there is accordingly obtained:
(a) cis,cis-9,12-octadecadienoic acid, 2-(o-methylphenyl)-hydrazide (as an oil);
(b) cis,cis-9,12-octadecadienoic acid, 2-(2,6-dichlorophenyl)-hydrazide, (as an oil);
(c) cis,cis-9,12-octadecadienoic acid, 2-(o-chlorophenyl)-hydrazide (as an oil).

EXAMPLE 4

Repeating the procedure of Example 3, but using in place of the linoleic acid used therein, an approximately equivalent amount of oleic acid there are accordingly obtained as final products:
(a) cis-9-octadecenoic acid, 2-(o-methylphenyl)-hydrazide (as an oil);
(b) cis-9-octadecenoic acid, 2-(2,6-dichlorophenyl)-hydrazide; and
(c) cis-9-octadecenoic acid, 2-(o-chlorophenyl)-hydrazide.

EXAMPLE 5 cis,cis-9,12-octadecadienoic acid, 2-[β-(3-indolylethyl)]-hydrazide

Repeating the procedure of Example 1, but using in place of the benzylhydrazine dihydrochloride used therein, an approximately equivalent amount of β-(3-indolylethyl)-hydrazine, there is accordingly obtained the title compound.

Repeating the procedure of this example but using in place of the β-(3-indolylethyl)-hydrazine, an approximately equivalent amount of each of the following hydrazines in free form or as a hydrochloric acid addition salt thereof:
(a) 1-indanylhydrazine;
(b) (d,l)-α-methylbenzyl-hydrazine;
(c) α-(p-methylbenzyl)-benzyl-hydrazine;
(d) 2-[α(p-methylbenzyl)-p-methylphenylethyl]-hydrazine;
(e) p-biphenylyl-hydrazine; and
(f) p-benzylphenyl-hydrazine
there is accordingly obtained:
(a) cis,cis-9,12-octadecadienoic acid, 2-(1-indanyl)-hydrazide;
(b) cis,cis-9,12-octadecadienoic acid, 2-(α-methylbenzyl) hydrazide;
(c) cis,cis-9,12-octadecadienoic acid, 2-[α-(p-methylbenzyl)-benzyl]-hydrazide;
(d) cis,cis-9,12-octadecadienoic acid, 2-[α-(p-methylbenzyl)-p-methylphenylethyl]-hydrazide;
(e) cis,cis-9,12-octadecadienoic acid, 2-(p-biphenylyl)-hydrazide; and
(f) cis,cis-9,12-octadecadienoic acid, 2-(p-benzylphenyl)-hydrazide.

EXAMPLE 6

Repeating the procedure of Example 5, but using in place of the linoleic acid used therein, an approximately equivalent amount of oleic acid there are accordingly obtained as final products the oleic acid hydrazide analogs of each of the compounds I enumerated therein.

What is claimed is:

1. A compound which is a hydrazide of the formula:

$$A-\overset{O}{\underset{\|}{C}}-NH-NH-R$$

wherein

A is the residue of an unsaturated fatty acid minus the carboxylic function and has from 7 to 23 carbon atoms and has from 1 to 4 ethylenically unsaturated positions; and R is:
(a) an aralkyl radical of the structure $$-\underset{R^3}{\underset{|}{CH}}-(CH_2)_g- \text{(aryl with } R^1, R^2\text{)}$$

wherein g is 0 or 1;
wherein
$R^1$ is a hydrogen atom, halo having an atomic weight of from about 19 to 80, alkoxy having from 1 to 3 carbon atoms; or alkyl having from 1 to 3 carbon atoms;
$R^2$ is a hydrogen atom, alkyl having from 1 to 3 carbon atoms, alkoxy having from 1 to 3 carbon atoms, or halo having an atomic weight of from about 19 to 36; and
$R^3$ is a benzyl radical of the formula (iii)

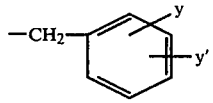 (iii)

wherein
y is a hydrogen atom, halo having an atomic weight of from about 19 to 80, alkoxy having from 1 to 3 carbon atoms, or alkyl having from 1 to 3 carbon atoms; and
y' is a hydrogen atom, alkoxy having from 1 to 3 carbon atoms, alkyl having from 1 to 3 carbon atoms, or halo having an atomic weight of from about 19 to 36;
or R is:
(b) a phenyl radical of the structure

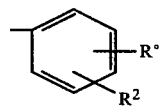

wherein
$R^2$ is as defined above, and
$R^0$ is a hydrogen atom, halo having an atomic weight of from about 19 to 80, alkyl having from 1 to 3 carbon atoms; alkoxy having from 1 to 3 carbon atoms; or a radical of the structure $R^f$:

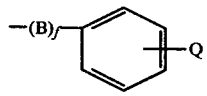

in which
B is —CH$_2$— or —O—;
f is 0 or 1; and
Q is a hydrogen atom, halo having an atomic weight of from about 19 to 80, alkoxy having from 1 to 3 carbon atoms, or alkyl having from 1 to 3 carbon atoms; or R is:
(c) an indolyl radical of the structure:

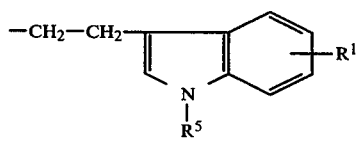

wherein
$R^1$ is as defined above, and
$R^5$ is a hydrogen atom, alkyl having from 1 to 8 carbon atoms or benzyl (unsubstituted);
or R is (d) a benzocycloalkyl nucleus of the structure:

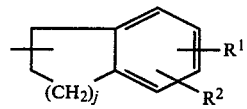

wherein
$R^1$ and $R^2$ are as defined above; and
j is a whole integer of from 1 to 4; or a non-toxic pharmaceutically acceptable acid addition salt thereof.

2. A compound of claim 1 in which R is a type (a).
3. A compound of claim 1 in which R is of type (b).
4. A compound of claim 1 in which R is of type (c).
5. A compound of claim 1 in which R is of type (d).
6. A compound of claim 2 in which g is 0.
7. A compound of claim 2 in which g is 1.
8. A compound of claim 3 in which $R^0$ is a radical of the structure

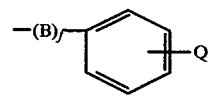

in which B, f and Q are as defined.
9. A compound of claim 1 in which A is of either the types (A1) having the structure:

$$CH_3{-}(CH_2)_r{-}(CH{=}CH)_s{-}(CH_2)_t{-}$$

or (A2) having the structure

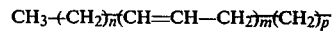

in which r is a whole integer of from 1 to 10, s is a whole integer of from 1 to 4, and t is a whole integer of from 4 to 9;
n is a whole integer of from 1 to 4,
m is a whole integer of from 2 to 4,
and p is a whole integer of from 2 to 7.
10. A compound of claim 9 in which A is of type (A1).
11. A compound of claim 10 in which A is the residue of oleic acid.
12. A compound of claim 10 in which A is the residue of palmitoleic acid.
13. A compound of claim 9 in which A is of type (A2).
14. A compound of claim 13 in which A is the residue of linoleic acid.
15. A compound of claim 13 in which A is the residue of linolenic acid.
16. The compound of claim 11 which is cis-9-octadecenoic acid, 2-(o-methylphenyl)-hydrazide.
17. The compound of claim 14 which is cis,cis-9,12-octadecenoic acid, 2-(o-methylphenyl)-hydrazide.
18. The compound of claim 14 which is cis,cis-9,12-octadecadienoic acid, 2-(2,6-dichlorophenyl)-hydrazide.
19. The compound of claim 15 which is cis,cis-9,12-octadecadienoic acid, 2-(o-chlorophenyl)-hydrazide.
20. A compound of claim 9 in which the hydrogen atoms of each unsaturated position are in the cis configuration.
21. A method of reducing the cholesterol ester content of an arterial wall in a mammal in need of such treatment, comprising administering to said mammal a cholesterol ester-reducing amount of a compound which is a hydrazide of the formula:

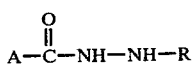

wherein
A is the residue of an unsaturated fatty acid minus the carboxylic function and has from 7 to 23 carbon atoms and has from 1 to 4 ethylenically unsaturated positions; and
R is:
(a) an aralkyl radical of the structure

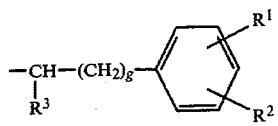

wherein g is 0 or 1;
wherein
$R^1$ is a hydrogen atom, halo having an atomic weight of from about 19 to 80, alkoxy having from 1 to 3 carbon atoms; or alkyl having from 1 to 3 carbon atoms;
$R^2$ is a hydrogen atom, alkyl having from 1 to 3 carbon atoms, alkoxy having from 1 to 3 carbon atoms, or halo having an atomic weight of from about 19 to 36; and
$R^3$ is (i) a hydrogen atom, a phenyl radical of the structure ii):

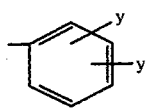

wherein
y is a hydrogen atom, halo having an atomic weight of from about 19 to 80, alkoxy having from 1 to 3 carbon atoms, or alkyl having from 1 to 3 carbon atoms; and
y' is a hydrogen atom, alkoxy having from 1 to 3 carbon atoms, alkyl having from 1 to 3 carbon atoms, or halo having an atomic weight of from about 19 to 36; or a benzyl radical of the formula (iii)

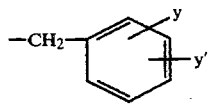

wherein y and y' are as defined above; or iv) alkyl having from 1 to 8 carbon atoms; or R is:
(b) a phenyl radical of the structure

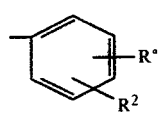

wherein
$R^2$ is as defined above, and $R^0$ is a hydrogen atom, halo having an atomic weight of from about 19 to 80, alkyl having from 1 to 3 carbon atoms; alkoxy having from 1 to 3 carbon atoms; or a radical of the structure $R^f$:

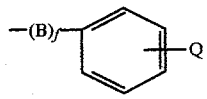

in which
B is $-CH_2-$ or $-O-$;
f is 0 or 1; and
Q is a hydrogen atom, halo having an atomic weight of from about 19 to 80, alkoxy having from 1 to 3 carbon atoms, or alkyl having from 1 to 3 carbon atoms; or R is:
(c) an indolyl radical of the structure:

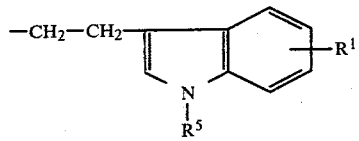

wherein
$R^1$ is as defined above, and
$R^5$ is a hydrogen atom, alkyl having from 1 to 8 carbon atoms or benzyl (unsubstituted); or
R is (d) a benzocycloalkyl nucleus of the structure:

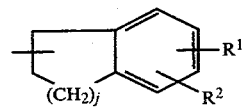

wherein
$R^1$ and $R^2$ are as defined above; and
j is a whole integer of from 1 to 4; or a non-toxic pharmaceutically acceptable acid addition salt thereof.

22. A method of claim 21 in which the compound is cis-9-octadecenoic acid, 2-(o-methylphenyl)-hydrazide.

23. A method of claim 21 in which the compound is administered orally.

24. A method of claim 21 in which the compound is administered in an amount of from about 100 milligrams to about 5,000 milligrams daily.

25. A method of claim 21 in which the compound is administered in an amount of about 100 milligrams to about 2,000 milligrams daily.

26. A pharmaceutical composition suitable for reducing the cholesterol ester content of an arterial wall of a mammal comprising a cholesterol ester-reducing effective amount of a compound of claim 1 and a nontoxic pharmaceutically-acceptable carrier.

27. A composition of claim 26 in solid form.

28. A composition of claim 26, in which the compound is present in an amount of from about 25 to 2,500 milligrams.

29. A compound of claim 28 in which the compound is cis-9-octadecenoic acid, 2-(o-methylphenyl)-hydrazide.

* * * * *